US010178864B2

(12) United States Patent
Boucher

(10) Patent No.: US 10,178,864 B2
(45) Date of Patent: Jan. 15, 2019

(54) PORTABLE ORGAN PERFUSION SYSTEM

(71) Applicant: Gary Boucher, Springhill, LA (US)

(72) Inventor: Gary Boucher, Springhill, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 261 days.

(21) Appl. No.: 15/124,209

(22) PCT Filed: Mar. 7, 2015

(86) PCT No.: PCT/US2015/019329
§ 371 (c)(1),
(2) Date: Sep. 7, 2016

(87) PCT Pub. No.: WO2015/138263
PCT Pub. Date: Sep. 17, 2015

(65) Prior Publication Data
US 2017/0013828 A1      Jan. 19, 2017

Related U.S. Application Data

(60) Provisional application No. 61/950,060, filed on Mar. 8, 2014.

(51) Int. Cl.
*A01N 1/02* (2006.01)
(52) U.S. Cl.
CPC ........... *A01N 1/0247* (2013.01); *A01N 1/021* (2013.01)

(58) Field of Classification Search
CPC .............................. A01N 1/0247; A01N 1/021
See application file for complete search history.

(56) References Cited

U.S. PATENT DOCUMENTS

| | | | |
|---|---|---|---|
| 5,338,662 A | 8/1994 | Sadri | |
| 2001/0031459 A1* | 10/2001 | Fahy | A01N 1/02 435/1.3 |
| 2004/0031756 A1* | 2/2004 | Suzuki | A61M 1/28 210/646 |
| 2004/0058432 A1* | 3/2004 | Owen | A01N 1/02 435/284.1 |
| 2005/0236329 A1* | 10/2005 | Brotherton | A61M 1/3472 210/645 |

OTHER PUBLICATIONS

International Search Report Corresponding to PCT/US2015/019329 dated Jul. 30, 2015.
Written Opinion Corresponding to PCT/US2015/019329 dated Jul. 30, 2015.

* cited by examiner

*Primary Examiner* — Michael L Hobbs
(74) *Attorney, Agent, or Firm* — Davis & Bujold PLLC; Charles Holoubek

(57) ABSTRACT

A profusion system for a mammalian organ comprising a first and a second pump to propel perfusion fluid through one of a closed fluid circuit system and a selectively closeable fluid circuit system that includes an organ artery and an organ vein, a filter cartridge bank consisting of a plurality of filtration cartridges, and a first and a second fluid reservoir.

14 Claims, 15 Drawing Sheets

PORTABLE ORGAN PERFUSION SYSTEM

CROSS REFERENCE TO RELATED APPLICATIONS/PRIORITY

This application claims priority to U.S. Provisional Patent Application No. 61,950,060 filed on Mar. 8, 2014.

FIELD OF THE INVENTION

This portable perfusion system relates to the equipment and method of preserving human or animal organs ex vivo, while monitoring and controlling the flow of perfusion fluid through the organ being preserved.

BACKGROUND OF THE INVENTION

For several years interest has grown in the concept of maintaining organs in viable and stable condition outside the human host for the purpose of extending the options for transplantation. New methods of flowing chemically enriched fluids though human organs have shown efficacy in extending organ life ex vivo. Perfusion is the practice of pumping a blood-similar fluid into the artery and out through the vein of the organ in much the same way as a heart pumps blood through the organ to maintain function.

This portable perfusion system could be used to transport organs from one location to another, especially where the journey requires days or even weeks. The ability to transport organs over longer time spans would be especially valuable in emerging third-world nations that do not have a strong transportation infrastructure. For the longer preservation times to be realized, the perfusion system must have the highest possible reliability, efficiency, and control.

SUMMARY OF THE INVENTION

This invention pertains to a portable perfusion system, which will result in an improved and more stable flow of fluid through the organ outside the host organism. Also, modularity of pre-sterilized system components will facilitate the quick cycling from use with one organ to the next with minimal downtime. This modularity will greatly reduce both the time spent on refurbishing the system to handle the next organ, and much of the need to sterilize individual components.

One highly integral part of the perfusion systems is filtration. Filtration may be required down into the low micron range to remove cellular materials and pathogenic organisms from the perfusion fluid to prevent recirculation of these contaminates. For an extended use perfusion system, filters may need to be replaced while the equipment continues to operate. Reconnecting the inlet side of a filter is generally not as critical of a task as reconnection of the outlet side of the filter, due to any contamination on the inlet side of the filter passing into, and thus being trapped by the filter. However, any contamination introduced during filter replacement on the outlet side of the filter can be critical, as it might potentially be allowed to circulate through the organ. This risk is addressed in the disclosed system.

Filtration cartridges offer another problem to the system designer due to the inclusion of large air bubbles into the system which can potentially be harmful to the organ. Also, during the filter exchange operation, sudden and varied changes in pressure may be noted in the fluid lines downstream from the filtration which in-turn may also damage the organ. These risks are addressed in the disclosed system In some of the disclosed perfusion system embodiments, filtration is purposefully not located either close to, or immediately before, where the fluid enters the organ. Although bubble traps may be employed in such an arrangement, a bubble-free flow is more easily obtained if large bubbles generated by filter replacement or new filter initiation are allowed to be expelled into a reservoir incorporating a venting mechanism prior to the fluid entering the organ. Therefore, in many of the disclosed embodiments, the filtration is placed early in the sequence, prior to the fluid entering a reservoir.

A typical filter cartridge in the art may have a differential pressure varying from 1 to 3 PSI when new, but as the filter loads with filtered material, the differential pressure of operation may increase to much higher values, for example, 50 to 90 PSI. Such increases in filter pressure offer a challenge for a single-pump system that must carefully control the arterial pressure to the organ being perfused. Since the pump pressure in a single-pump system must supply both the large differential filter pressure and also the highly regulated arterial pressure, it becomes difficult to maintain control of arterial pressure as desired.

Disadvantageously, in a single pump system if the pump is placed next to the artery of the organ, the pump must draw the fluid through the filter system using a vacuum, which in-turn limits the differential pressure to one atmosphere, or approximately 14.7 PSI. Limiting the differential pressure from inlet to outlet can result in failure to obtain the full rate of flow of fluid through the filter system, as filter loading occurs.

These problems can be avoided, and considerably better regulation can be provided by using a two-pump system. The disclosed perfusion system describes such a system for use in organ perfusion, and eliminates pressure and bubble problems by performing filtration upstream from the main pump that regulates organ arterial pressure.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
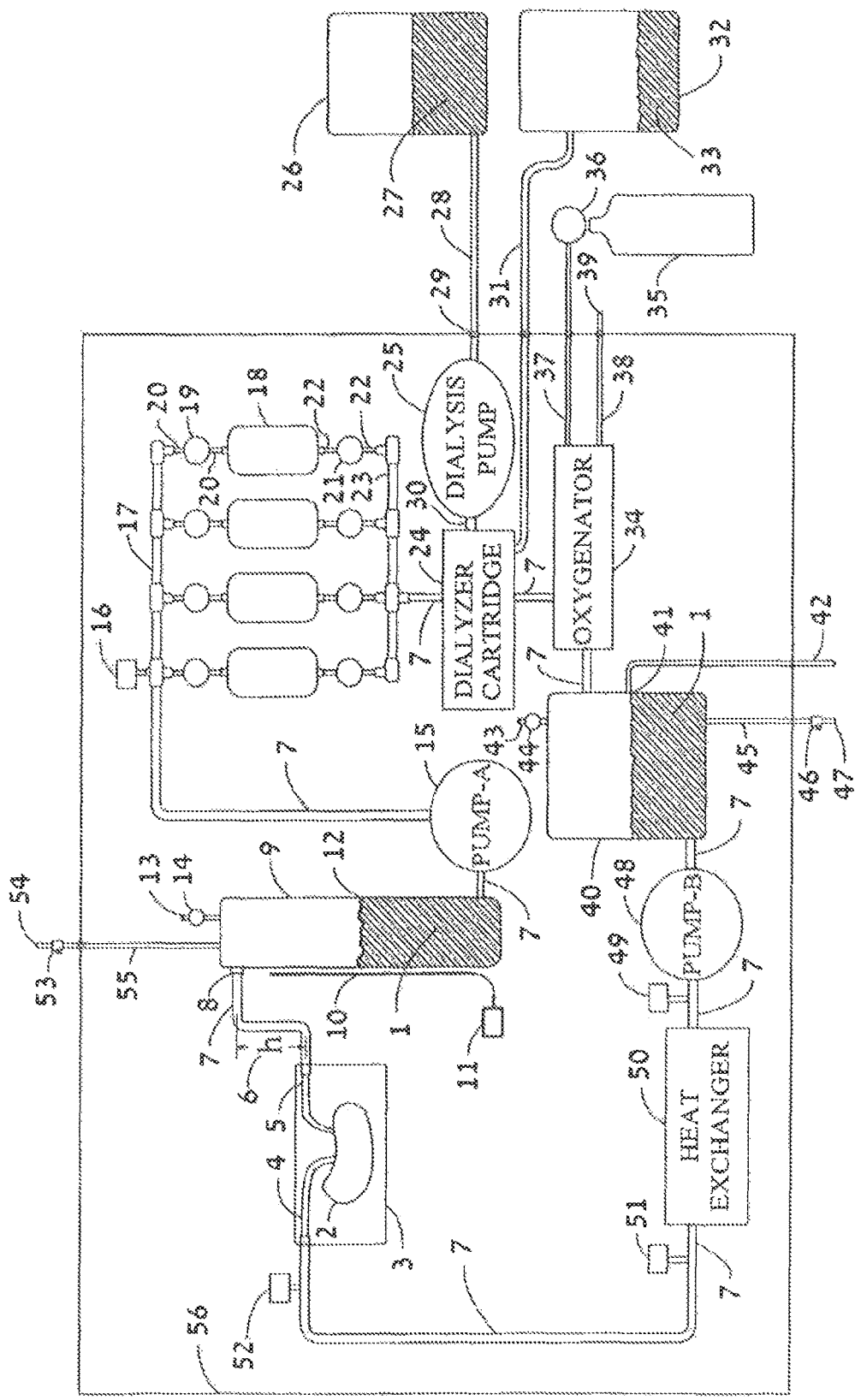
FIG. 1 is a diagrammatic representation of an embodiment the perfusion system according to the present invention.

Turning now to FIG. 1, a brief description concerning the various components of the present invention will now be briefly discussed. As can be seen in this embodiment, perfusion fluid (1) flows out from the organ (2) located in an organ chamber (3) through the vein of the organ (5) and into connection tubing (7) that directs the perfusion fluid (1) in a fluid circuit upward to an upper inlet port (8) on reservoir-A (9). To regulate the venial pressure, the height of entry 'h' (6) into reservoir-A can be controlled by placing the inlet port of reservoir-A (8) at such a level as to create a standpipe effect holding constant back pressure against the organ (2), typical values of 'h' can range from 0 to 15 inches. With this simple pressure regulator, such a value of 'h' will create a backpressure on the organ (2) of from 0 to approximately 30 mm of Hg.

Reservoir-A (9), through an electronic control system (132), described later and illustrated in FIG. 15, maintains a nearly fixed level of perfusion fluid (1), by controlling the rate of pumping by pump-A (15). Liquid level indication can be furnished by a variety of detection schemes commonly employed, but not limited to, capacitive, optical, weight, or pressure. If the fluid level falls below the desired set level (12), pump-A (15) slows its pumping rate, pumping less fluid from reservoir-A (9) than is entering from the organ (2) via the upper port (8). If the fluid level in reservoir-A (9) rises above the set-point level (12), pump-A (15) will automatically pump at a faster rate to lower the fluid level of reservoir-A (9) back toward the set point (12). Level detection is shown in FIG. 1 using a capacitive strip sensor (10) placed in contact alongside reservoir-A (9), that is connected to a level sensing unit (11) which furnishes an electrical signal back to the electronic control system (132). This closed feedback model maintains a nearly fixed level of fluid in reservoir-A (9). From pump-A (15), the fluid flows into a manifold (17) via system connection tubing (7), where it is ported out to a series of clampable tubes (20), each passing through tube clamping assemblies (19).

After passing through the inlet clamping assembly (19), the fluid is directed into the filter cartridge or cartridges (18) and then out through a clampable tube, or tubes (22). In a similar manner to the inlet tubes (20), these outlet tubes (22) also run through one or more clamping assemblies (21). The fluid flow from all active filters (18) recombines in a second manifold (23) to be passed to the dialyzer cartridge (24) via system connecting tubing (7). The pressure of the fluid entering the dialyzer cartridge (24) has lowered to near ambient levels, which results in the pressure reading taken by the inlet manifold pressure transducer (16) being approximately the same as the filter cartridge (18) differential pressure from inlet to outlet.

To facilitate the availability of fresh filter cartridges (18) without the necessity of removing and replacing such cartridges during operation, all necessary cartridges (18) required may be loaded prior to the onset of system operation. A typical embodiment of the perfusion system would include 4 filter cartridges (18). Using electromechanical, pneumatic, or hydraulic means, both aforementioned clamping assemblies (19, 21) are provided to control the flow to and from each individual filter cartridge (18). Thus, by closing either the inlet clamping assembly (19) or the outlet clamping assembly (21), the flow can be stopped though a particular filter cartridge (18). In this way, certain cartridges may be used at any time while others not in use may be isolated. Double-clamping each filter (18), once at the inlet and once at the outlet, will prevent trapped aged fluid from migrating through the perfusion system and generating contamination, although a single clamping assembly (19) or (21) can be used to completely stop the flow of perfusion fluid (1). Pump-A (15) should optimally possess a relatively high pressure capability, large enough to obtain the maximum life from each filter cartridge (18). The maximum pressure capacity of pump-A (15) should typically range from 35 to 90 PSI.

Dialysis is used for the removal of various toxins that can build up in the perfusion fluid (1) during perfusion. The dialyzer (24) may be, in some embodiments, an identical unit to those used in routine human dialysis treatments, such as the Nikkiso FDX-150GD polycarbonate hollow-fiber dialyzer, or the Purema model B-14P hollow fiber polyethersulfone dialyzer. A separate dialysis fluid pump (25) is preferably provided to push fresh dialysis fluid (27) through the dialyzer (24). Fresh dialysis fluid (27) is maintained in a reservoir (26) preferably external to the perfusion system enclosure (56), and flows via a transfer tube (28) into the dialysis fluid pump (25), as it passes through the enclosure (56) wall at pass-through fittings (29). Preferably all tubing entering or exiting the enclosure (56) will have such pass-through fittings (29) to seal the perfusion enclosure (56) and yet allow fluids to pass. After exiting the dialysis fluid pump (25), the dialysis fluid passes into a tube (30) carrying it to the dialyzer (24). After exiting the dialyzer, the used dialysis fluid (33) returns to a reservoir of depleted dialysis fluid (32) through a return tube (31) also passing through the enclosure (56).

The speed and/or duty-cycle of the dialysis fluid pump (25) can easily be electronically connected or otherwise brought under the control of the electronic control system (132) responsible for other perfusion system functions. Although depicted in FIG. 1 as being located inside the perfusion system enclosure (56), the dialysis fluid pump (25) can be located outside the enclosure (56). The two dialysis fluid reservoirs (26, 32) can also be located either inside or outside of the enclosure (56). Locating these reservoirs (26, 32) inside the enclosure (56) would afford better temperature control of the circulating perfusion fluid (1), since the perfusion fluid comes into virtual contact with the dialysis fluid as dialysis occurs. The negative aspect to the procedure of locating the dialysis fluid inside the system enclosure (56) is in the bulk of fluid to be contained for extended perfusion system operation. However, since only a small amount of toxin need be removed from an organ, compared to what must be removed for a human patient undergoing routine dialysis treatments, the size may be greatly reduced and/or the life of a dialyzer (24) may be greatly extended, and thus allow enough dialysis fluid for extended use of the perfusion system to be contained in the enclosure (56).

The perfusion fluid (1) exiting the dialyzer (24) flows into an oxygenator (34) via connection tubing (7), where oxygen is introduced to the perfusion fluid (1). Usually, this is accomplished by the use of gaseous oxygen that is passed from a high pressure O2 tank (35) via a pressure regulator (36) into, and then out of, the oxygenator (34), via O2 tubing (37, 38). Numerous oxygenator devices of different types, sizes, and capacities are marketed today for a wide range of medical and research use. A pediatric oxygenator such as the Sorin KiDS D101 can be used, and will have more oxygenating capacity than required, comparing the oxygen requirements of an organ undergoing perfusion to the needs of a small child.

From the oxygenator (34), the perfusion fluid (1) flows into reservoir-B (40). This second perfusion fluid reservoir does not require as precise fluid level monitoring due to the fact that only the overall perfusion fluid (1) volume dictates the level of perfusion fluid (1) in reservoir-B (40). However, for system feedback of overall fluid level, sensing may be employed and recorded by the electronic control system (132).

Replenishment of perfusion fluid (1) may be done anywhere in the system, but is preferably added to the system by flowing new perfusion fluid into reservoir-A (9). In this way, new perfusion fluid (1) is filtered before returning it to the organ (2) to remove contaminates. The overall perfusion fluid (1) quantity can be monitored by observing the perfusion fluid (1) level in reservoir-B (40). Since reservoir-A (9) preferably has its fluid level automatically controlled to the set point (12), reservoir-A (9) would then maintain essentially the same volume of perfusion fluid (1). Any added perfusion fluid (1) would then, therefore, raise the volume of perfusion fluid (1) in reservoir-B (40) only. With reservoir-A (9) automatically maintaining a constant volume, monitoring the level of perfusion fluid (1) in reservoir-B (40) is sufficient to monitor the overall quantity of perfusion fluid (1) in the system.

Perfusion fluid (1) is drawn from reservoir-B (40) by a second pump, pump-B (48). Leaving pump-B (48), the fluid enters the heat exchanger (50) where the electronic control system (132) adjusts the temperature of the perfusion fluid (1) by either heating or cooling of the fluid (1) to the desired temperature. A unique approach to both heating and cooling of the fluid (1) by the same device is introduced as the preferred embodiment for temperature control of the perfusion fluid (1), by using a Peltier semiconducting module. The advantage of using direct or indirect heating and cooling of the perfusion fluid (1) by such semiconductor means is in the ability to control the temperature directly through electronic means, and to be capable of making fast changes if necessary. Although heating of the perfusion fluid (1) can be performed via resistance-type heating elements, refrigeration normally requires far more equipment and power, which, while still considered part of the disclosed invention, is not easily implemented in a portable device.

The pressure differential across the heat exchanger (50) should be negligible, allowing pump-B (48) to easily set the overall arterial pressure of the organ (2). Measurements of the arterial pressure with the arterial pressure transducer (52) allow the electronic control system (132) to have constant pressure feedback. This arterial pressure transducer (52) should be located at or near the level of the organ's artery (4), so as to minimize pressure reading differences due to the standpipe effect. Current state of the art pressure transducers such as would be used clinically on an intravenous central line for constant blood pressure measurement can be used, with the transducer's output being fed to the electronic control system (132). The TruWave PX600P pressure transducer is an example of one such pressure transducer (52) typically used in monitoring blood pressure via a central line.

If the arterial pressure drops below the desired set point, pump-B (48) runs faster increasing the fluid flow rate. If the arterial pressure is too high, pump-B (48) slows to allow a lower rate of fluid flow, and thus a lower arterial pressure entering the artery (4) of the organ (2). Therefore, pump-B (48) sets the perfusion fluid flow rate through the entire perfusion system, while reservoir-A (9) and pump-A (15) simply provide fluid volume cushioning for long-term matching of fluid quantities passing through the perfusion system. Although pump-A (15) and pump-B (48) may, at any given instant, have slightly different flow rates, as the perfusion system adjusts to system chances such as filter switching, the overall average perfusion fluid rate for both pumps (15, 48) should be substantially identical under normal operation of the perfusion system. It should be noted here that without reservoir-A (9) incorporated into the system, both pumps (9, 48) would have to run at exactly the same rate to prevent pressure spikes being formed in various locations of the system.

The two-pump system described in this invention allows for extreme differential pressure variations with the filter cartridges (18). As a new unloaded filter (18) is employed, the differential pressure may be around 1 to 2 PSI, but as filter loading occurs, the differential pressures across the filters can grow to perhaps 80 to 100 PSI. Attempting to use only pump-A (15) and reservoir-A (9) alone could result in having to control delicate arterial pressure levels on top of a 100 PSI filter backpressure at certain times. Also, when filter cartridges (18) are phased in, dangerous pressure spikes can be noted when switching from a high differential pressure (old) filter (18) to a low differential pressure (new) filter (18). Such pressure spikes are due to the reaction time of the electronic control system (132) and the mechanical pump's (15) inertia.

As an example of a one-pump system creating potential problems, consider pump-A (15) producing 80 PSI of backpressure on an old end-of-life filter cartridge (18). If suddenly the clamping assemblies (19, 21) for a new yet unused filter cartridge (18) are opened, the now bypassed flow may only be opposed by a 2 PSI backpressure. The pressurized and expanded tubing and manifold components (7, 17, 20) running from pump-A (15) to the filter cartridges (18), plus the now lowered backpressure on pump-A (15) will create an overpressure before the perfusion system can bring the pressure spike under control via the electronic control System (132). Another cause of problems for smooth pressure control of the organ (2) is found in the fluctuations noted in introducing a new filter cartridge (18) that initially contains air, and must be flooded with perfusion fluid (1). For these and other reasons identified by the inventor the novel two pump perfusion system is employed.

In the perfusion system, temperature measurement is most critical at the point where the perfusion fluid (1) enters the organ's artery (4). In one embodiment, the entire perfusion system would be housed in a thermally insulated environment such as an airtight enclosure (56) where the ambient temperature matches as well as possible the temperature of the perfusion fluid (1) passing into the organ (2). In this way, very little heat is required to be added or removed from the fluid. Although temperature measurement can be easily taken at any location throughout the system, the preferred location for a single temperature sensor (51) is shown downstream from the heat exchanger. Improved temperature control can be obtained using an additional temperature sensor (49) upstream from the heat exchanger. This temperature sensor (49) can tell the electronic control system (132) the temperature of the perfusion fluid (1) before heat is added or removed, to better regulate how much heat need be exchanged.

Replenishment of perfusion fluid (1) can be accomplished by systematically adding new perfusion fluid (1) and allowing existing fluid (1) to gradually flow out of the perfusion system to be collected as waste. As mentioned earlier, new perfusion fluid (1) should preferably pass through filter cartridges (18) prior to entering into the organ (2). A preferred location to add fluid would be reservoir-A (9). This can be done by an entry port (54) for new fluid, whereby new fluid introduction can be handled by either a manual valve (53), or an automatic electrically-operated valve under the control of the electronic control system (132). Tubing (55) allows the new perfusion fluid (1) to flow into reservoir-A (9).

If new perfusion fluid (1) is added to reservoir-A (9), the fluid level in reservoir-A rises above the set point level (12). The level rise is sensed by the electronic control system (132), which in turn speeds up pump-A (15) to return reservoir-A (9) to the proper set point (12). This ultimately results in more fluid passing into reservoir-B (40) than is being pumped out of reservoir-B (40) by pump-B (48), since the rate of flow of pump-B (48) is only based on the desired arterial pressure, and is unrelated to the level of perfusion fluid (1) in reservoir-B. Therefore, adding perfusion fluid (1) to the system causes the level of fluid in reservoir-B (40) to increase, reflecting a higher overall perfusion fluid (1) volume. An overflow port (41) can be used to limit the volume of fluid (1) contained by reservoir-B. Overflow port (41) can also automatically pass fluid from reservoir-B (40) through a drain tube (42) as a waste product as replenishment occurs. Therefore, in such an embodiment the depth of perfusion fluid (1) found in reservoir-B (40) would never be greater than the height of the exit port (41) for the drain in reservoir-B (40). In this way the system's perfusion fluid (1) may be slowly replaced, maintaining the needed potency simply by adding new perfusion fluid (1) and allowing the excess perfusion fluid (1) to exit the port (41) as replenishment occurs.

Alternatively or additionally, a drain tube (45), along with a drain valve (46), under either manual, or electronic control system (132) control can be used to drain perfusion fluid (1) from the bottom of reservoir-B (40). This would allow quicker and more complete fluid replacement, but would need to be monitored carefully so as to prevent pump-B (48) from drawing air from an empty reservoir-B (40). This method of replenishment would allow a sizable portion or the perfusion fluid (1) to be replaced in one short cycle. Also, reservoir-A (9) could be allowed to temporarily operate at a lower set point (12) during replenishment under electronic control system (132) operation. However, in neither of these described replenishment methods can the entire fluid contents be replaced at any one point in time This would require the stoppage of flow to the organ (2), a generally undesirable situation.

Since reservoir-A and reservoir-B (9, 40) will need the ability to change their fluid volume, a breather is required on both. The reservoir-A vent (13) is connected to reservoir-A (9) through a filter (14) in the low micron range. A good choice would be a 1 to 2 micron filter. This can be a common syringe filter with the ability to limit contaminants and bacteria from entering the system. Reservoir-B (40) has a similar filter (44) and vent (43).

It is important to provide perfusion fluid (1) to the organ (2) at the proper temperature, which may vary from below ambient operating temperature to well above ambient temperature. This may be manually controlled by an operator, or more preferably regulated using the electronic control system (132). In either case the temperature will be sensed and heat removed or added to the perfusion fluid (1) to maintain the temperature at or near the desired set point via the heat exchanger (50). The disclosed perfusion system is contrary to current perfusion systems in the art which use electrical resistance heating and do not furnish the ability to cool the fluid being pumped. This heat only approach fails if the perfusion system is operated in an ambient temperature greater than the required fluid temperature, since only heat can be added in such systems.

Figure 2:
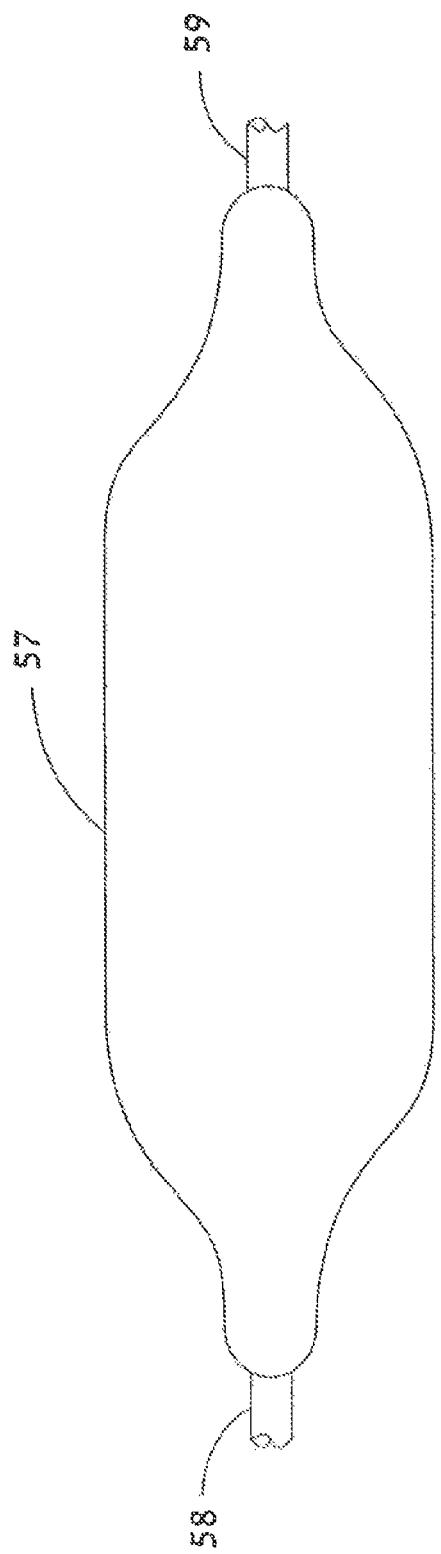
FIG. 2 is a plan view of a flexible bladder of the heat exchanger of FIG. 1.

FIG. 2 shows a flexible bladder (57) designed to transfer heat easily due to its nearly flat geometry yielding a large surface area. Such a bladder (57) could be on the order of 12 inches long, 4 inches wide and 0.250 to 0.375 inches in depth. An entry point to the bladder (59) allows perfusion fluid to enter from pump-B (48), and an exit port (58) allows the fluid to exit toward the organ (2). The bladder body (57) can be manufactured from plastic materials commonly used in medical tubing, but should be flexible enough to conform to a set of parallel metal plates (60) for optimizing heat flow. Although this bladder (57) could be made removable from the overall system through fluid path connections, the preferred embodiment would employ the heat exchanger bladder (57) as a sealed portion of the entire perfusion system's fluid path, and could be constructed of materials that can withstand the temperatures of autoclaving.

Figure 3:
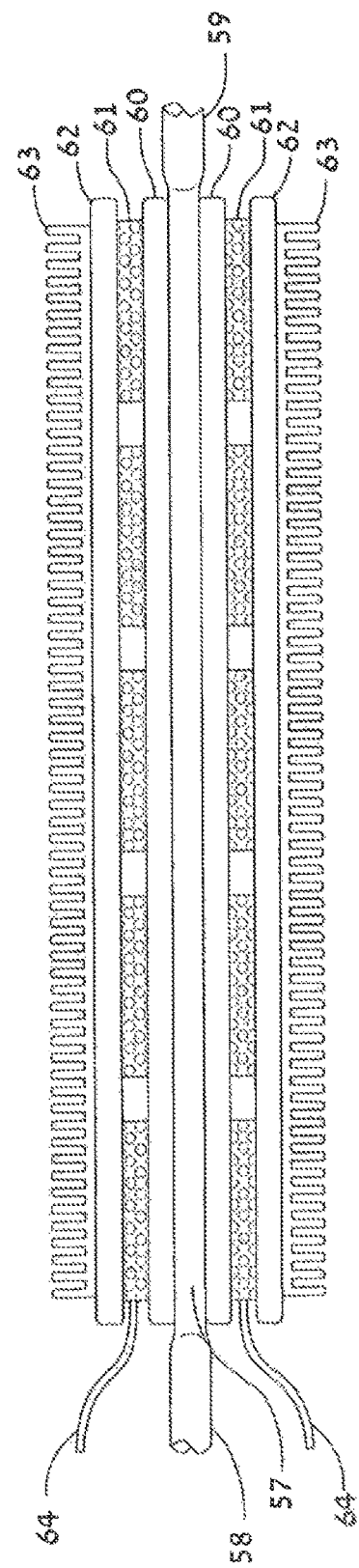
FIG. 3 is a sectional side view of the heat exchanger of FIG. 1.

A section of the complete heat exchanger (50) is shown in FIG. 3, including a side view of the bladder (57). In this preferred embodiment, heating and/or cooling is performed using a Peltier semiconductor heat pump. The Peltier arrays (61) are shown sandwiched between two heat-conductive metal plates (60, 62). This semiconductor heat pump system accepts current in either direction through wires (64), creating both hot and cold plates (60, 62). The determination of which plates (60, 62) are to be hot or cold is based on the direction of current flow through the Peltier device array (61), and is controlled by the electronic control system (132).

The metal inner plates (60) next to the bladder (57) transfers heat into or out of the perfusion fluid (1) by thermal conduction through the thin bladder material. The metal outer plates (62) are connected to sinks or sources of heat such as convective heat exchangers (heat sinks) (63) using air, water, or other moving streams of fluids, which may provide or accept heat. This method of pumping heat into or out of the perfusion fluid (1) is especially useful due to the concept that some systems may require chilling of the perfusion fluid (1) for periods, and heating of the same fluid at other times. Control over both direction and magnitude of heat transfer is initiated by the electronic control system (132), if not controlled manually.

It should be noted that the Peltier arrays (61) are preferably wired such as to have both inner plates (60) hot at the same time, or both inner plates (60) cold at the same time. In one embodiment, the bladder (57) may simply be inserted between the plates by the technician who sets up the system.

In the preferred embodiment, the two fixed inner plates (60) can be temporarily removed, lifted apart, or spread to allow easy insertion of the bladder (57).

Although filter cartridges (18) in theory can be changed while a perfusion system is in operation, a more preferred approach, and one less prone to contamination via foreign materials or outside organisms, would be to place all necessary filter cartridges (18) into the closed perfusion system prior to operation. Preferably one or more extra cartridges (18) would also be included as may be needed for unexpected delays in delivering the organ (2). While the perfusion fluid (1) can be allowed to flow into all filter cartridges (18) simultaneously, the preferred approach would be to have the option of clamping and unclamping the inlet and outlet tubes (20, 22) to each filter cartridge (18) as needed. Thus, system operation could begin with one or two filter cartridges (18) having unclamped inlet and outlet tubes (20, 22), while the other filter cartridges (18) are prevented from flowing by clamped tubes (20, 22).

It is undesirable to use any method of tube clamping whereby a full or partial failure of the system results in an inadvertent clamping or unclamping of the filter pathways. Thus, any electromechanical, pneumatic, or hydraulic method that can fail toward the unwanted condition should be avoided. Sudden opening of filter pathways after being closed for considerably long periods can release stagnant fluid trapped inside the previously used filter cartridge (18). Having unwanted closures can completely block the perfusion path resulting in catastrophic system failure. Therefore, it is highly preferable to have that the flow condition through all tubes (20, 22) carrying fluid to and from the filter cartridges (18) remain in a static condition should system failure of any type occur.

Figure 4:
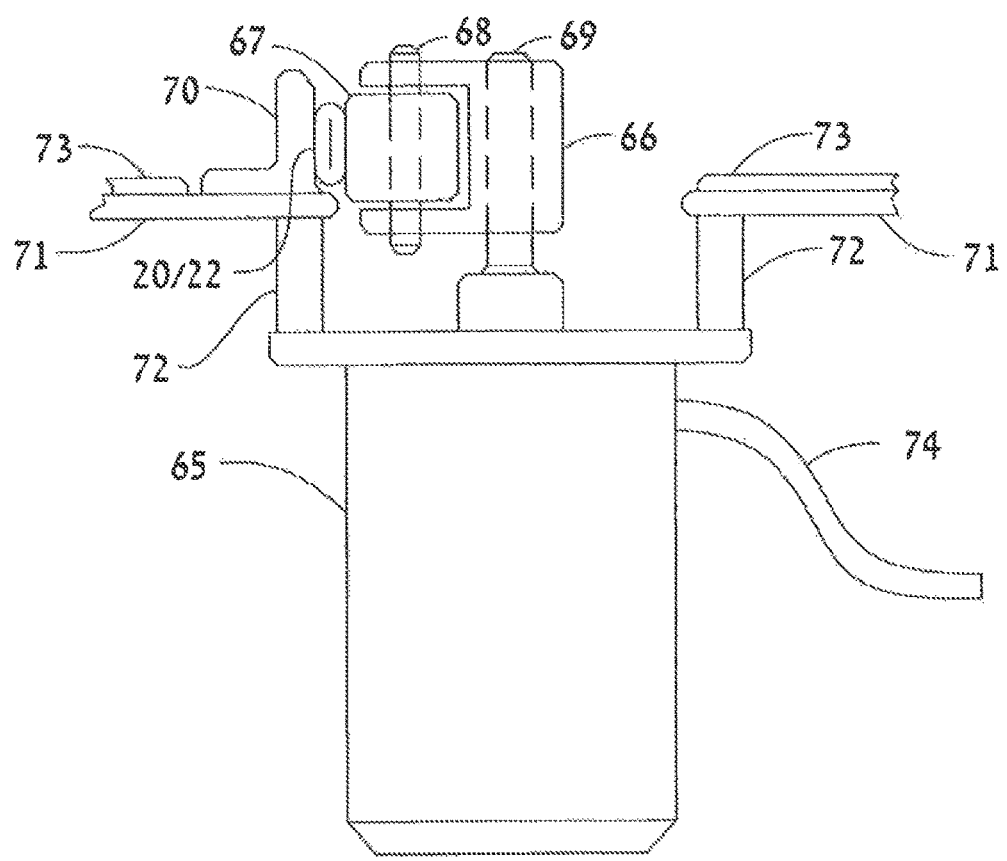
FIG. 4 is a side view of the tube clamping assembly of FIG. 1 shown in a closed position.

FIG. 4 shows a tube clamping assembly (19, 21) representing the inlet clamping mechanism (19) or the outlet clamping mechanism (21). This clamping mechanism consists of a cam (66), which is offset from a rotatable gearmotor shaft (69). The cam body (66) houses a roller (67) which freely revolves about a pin (68). The cam (66) is thus rotated by the geared stepping motor (65) preferably utilizing internal or external angular position feedback available through many stepping motor vendors. The repetitively collapsible filter fluid inlet or outlet tubes (20, 22), rest against backstops (70) and the cam rollers (67). When the cam assembly (66, 67, 68) is rotated such that the cam roller (67) is squeezing a tubing (20, 22) against the backstop (70), the fluid flow is completely stopped. When the cam assembly (66, 67, 68) is at virtually any other position, rotated by the gear motor (65), the specific tube (20, 22) returns to its original shape and the fluid is allowed to flow.

Figure 5:
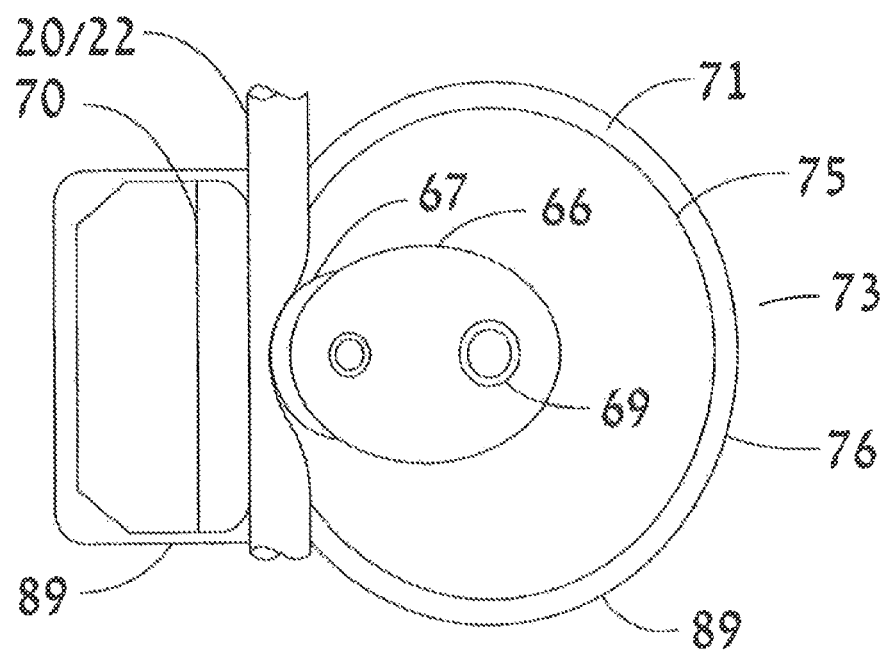
FIG. 5 is a plan view of the tube clamping assembly of FIG. 4.
Figure 6:
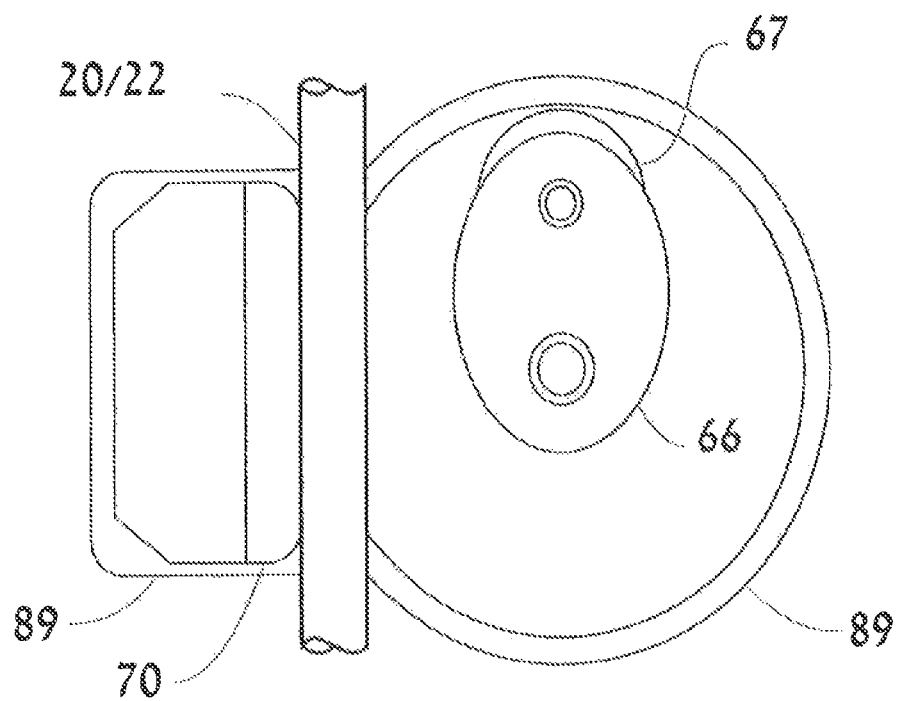
FIG. 6 is a is a plan view of the tube clamping assembly of FIG. 1 shown in an open position.

FIG. 5 shows a view of a clamping assembly (19, 21) looking into the gear motor shaft (69) showing the clamping assembly (19, 21) closed with no perfusion fluid (1) flowing. FIG. 6 shows a clamping assembly (19, 21) open allowing perfusion fluid to flow.

In a portable perfusion system, the designer must be keenly aware of two problems—cross pathogenic contamination between the organs (2) of two different hosts, and the time it takes to change from one organ undergoing perfusion to another. Turnaround times between organs should be short and free from the possibility of external and internal contamination. One solution to this problem would be to combine most necessary components of the perfusion system into one initially sealed and sterilized assembly, the prefabricated panel assembly shown in FIG. 7.

Figure 7:
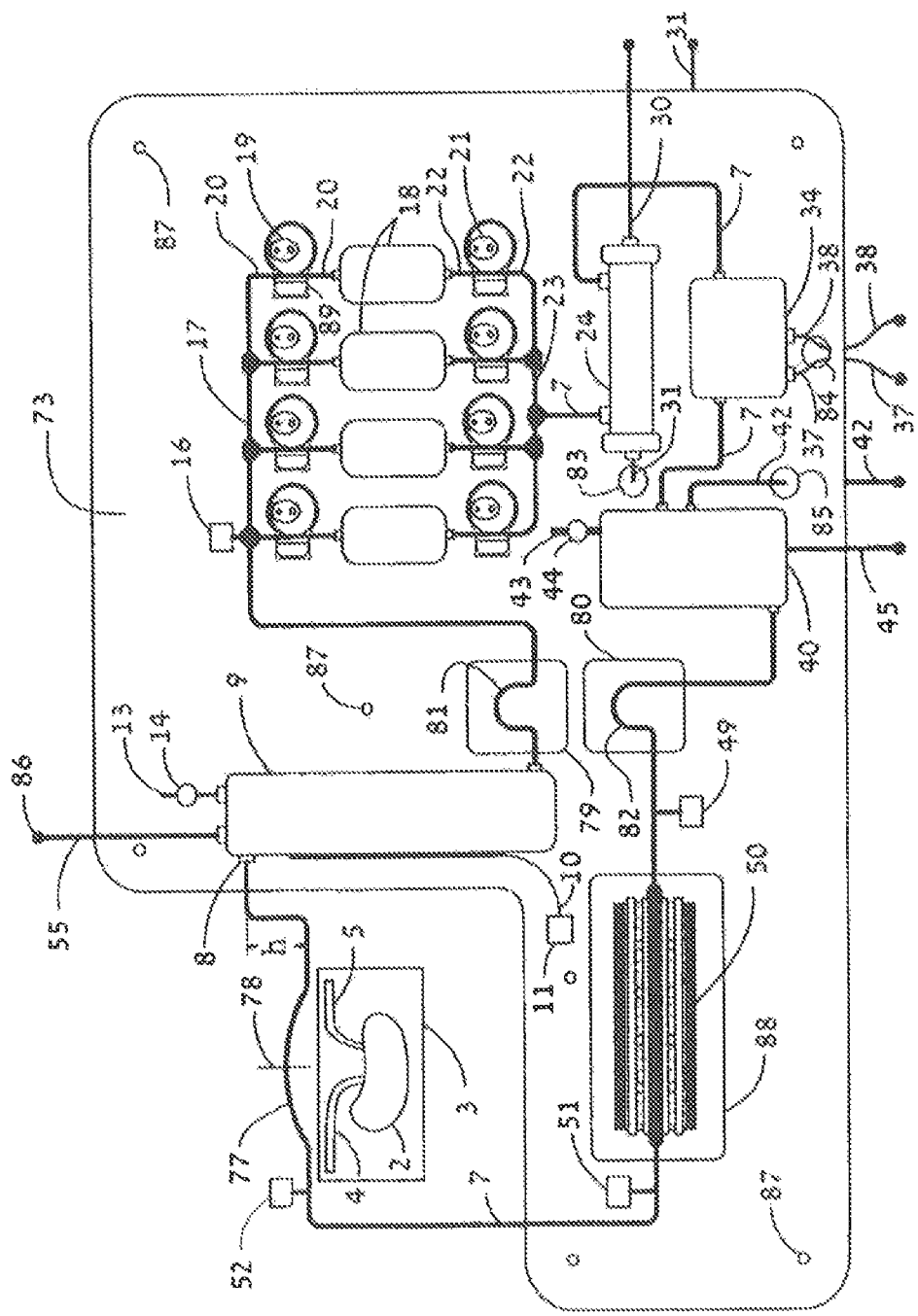
FIG. 7 is a diagrammatic representation another embodiment of the perfusion system according to the present invention, as a prefabricated panel assembly.

The geared stepping motors (65) are mounted to a structural panel (71) using spacers (72). FIG. 7 shows an easily-reloadable prefabricated panel assembly (73) containing most of the major perfusion system components consisting of a metal or plastic support panel or panels (73) that would mount flush and be fastened to the structural panel (71) that supports the clamping assemblies (19, 21). In this way, the prefabricated panel assembly's (73) set of pre-mounted components including the tubing (20, 22) to and from the filter cartridges (18) could simply lay into the spaces provided between the cam assemblies (66, 67, 68) and the backstops (70). The structural panel openings (75) and the prefabricated panel assembly opening (76) are shown in FIG. 5.

Multi-conductor sets of driving wires (74) are used to carry current and feedback information to and from the geared stepping motors (65). Driver circuits can rotate one or more cams assemblies (66, 67, 68) at any time under the control of the electronic control system (132). In either closed (FIG. 5) or open position (FIG. 6), the clamping assembly's cam assembly (66, 67, 68) will remain stationary due to the high gear ratio of the stepping motor (65), unless the gearmotor (65) is rotated electrically with stepped pulses. Accidental rotation is thus prevented without the proper sequence of steps to the motors (65) making unintended changes in the fluid flow highly unlikely. This scheme easily facilitates the mentioned large drop-in style prefabricated panel assembly panel (73) containing all disposable components necessary to do perfusion.

The thicker solid lines shown in FIG. 7 represent the system tubing associated with the main fluid path of the perfusion system. An extended length of plastic tubing forms an organ graft loop (77) that is provided for inline insertion of the organ to be perfused. The technician simply cuts the plastic tubing at a predetermined location (78) and grafts the artery (4) and vein (5) of the organ (2) onto the open ends of the cut tube loop (78). The organ (2) and connected tubing are then placed into the organ chamber (3). In a further embodiment, where the organ has multiple arteries (4) and veins (5) that require perfusion fluid (2), it is anticipated that the organ graft loop may branch into a number of tubes to provide a plurality of inlet tubes to attach to a plurality of arteries (4) of the organ (2) and a plurality of outlet tubes to attach to a plurality of veins (5) of the organ (2).

The prefabricated panel assembly base panel (73) comprises the mounting platform for the major system components including, but not limited to reservoir-A (9), pressure transducer (16), inlet manifold (17), filter cartridges (18), collapsible tubing for clamping assemblies (20, 22), outlet manifold (23), dialyzer (24), oxygenator (34), reservoir-B (40), heat exchanger (50), temperature sensors (49, 51) and the arterial pressure transducer (52). Though not shown in this embodiment, the prefabricated panel assembly support panel could house and support the organ chamber (3). All mounting of components onto the panel can be done with prefabricated standoffs, spacers, and mounting supports well established in the art. These supports allow the components to be mounted close to, but usually above the plane of the prefabricated panel assembly support panel (73). Alternately, system components can be mounted behind the prefabricated panel assembly support panel (73) if needed, where space is available.

Both pump-A (15) and pump-B (48) are preferably peristaltic pumps similar to the Cole Parmer Masterflex Series. The drive motors for these pumps are mounted behind the prefabricated panel assembly structural panel (73), with only the pumping heads extended through the prefabricated panel assembly panel openings (79, 80). Extra system tubing (7) in loops (81, 82) is provided to allow routing through the pump heads.

Main fluid path system tubing (7), and other support tubing such as dialysis fluid tubing (30, 31), and oxygen gas tubing (37, 38) may be run either in front, or behind the prefabricated panel assembly support panel (73). This is demonstrated in FIG. 7 in two instances. Dialysis fluid from the dialysis pump (25) is routed to the dialyzer (24) by the dialysis supply tubing (30), which in this embodiment is routed on top of the prefabricated panel assembly support panel (73). After the dialysis fluid is routed through the dialyzer (24) the used dialysis fluid (33) flows into the outlet tubing (31). This tubing runs through a panel opening (83) to return to the reservoir of depleted dialysis fluid (32). Another example of routing various tubes behind the prefabricated panel assembly panel (73) is seen where the oxygen supply and return tubing (37, 38) is routed through a prefabricated panel assembly panel opening (84). All entry and exit tubing associated with the prefabricated panel assembly panel (73), whether run behind or on top of the prefabricated panel assembly support panel (73) is extended beyond the boundaries of the support panel (73) with enough length as to easily facilitate connection to external systems.

Any tubing (55, 45, 42, 30, 31, 37, 38) that is to exit the prefabricated panel assembly for connection elsewhere can simply be capped, usually before autoclaving. An example of this is the fluid replenishment tube (55) which is capped at its termination (86). The tube (55), just prior to the termination, can be cut by the installer and fastened to outside equipment as necessary.

Due to its self-contained nature, the prefabricated panel assembly can be sterilized using an autoclave, and shipped in a sterile enclosure such as a plastic bag that is to be opened just prior to installation. Mounting holes (87) allow the prefabricated panel assembly to be quickly and securely fastened to the structural panel (71) and any other fastening locations or provided brackets required for stable mounting.

Figure 8:
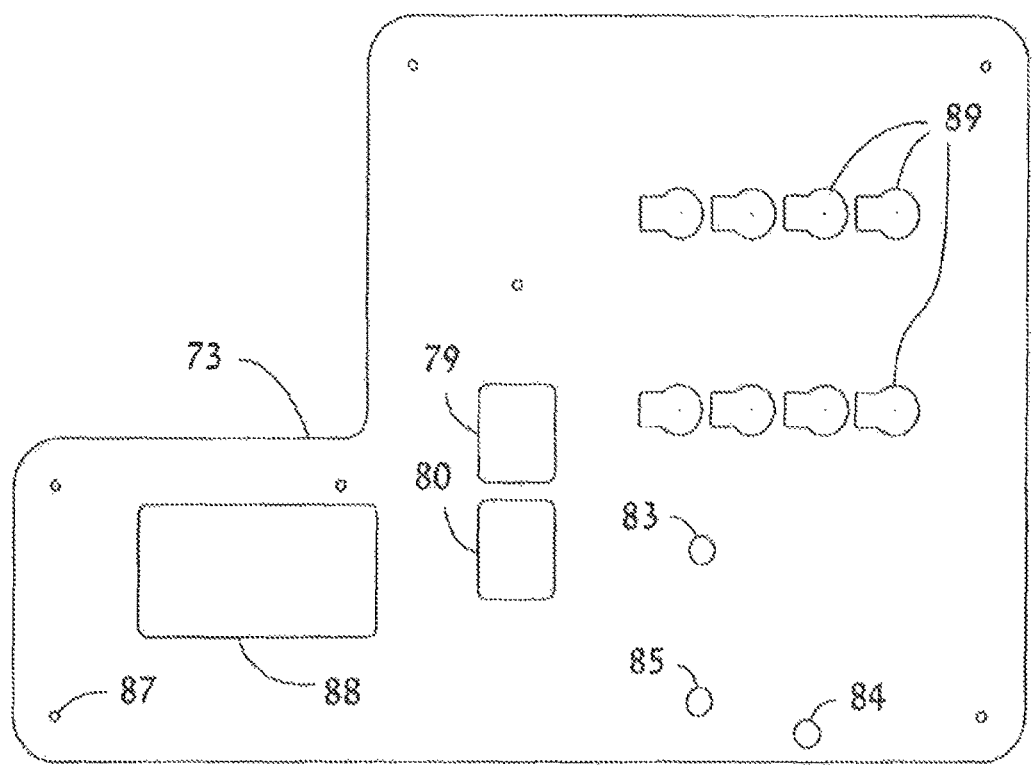
FIG. 8 is a is a plan view of a bare prefabricated panel of FIG. 7.

FIG. 8 shows the bare prefabricated panel assembly panel (73) with cutouts that can be used with a cylindrical prefabricated panel assembly-mounted reservoir-A (9) which can be mounted in front of the prefabricated panel assembly panel (73). Other prefabricated panel assembly embodiments using bag type reservoirs are shown in FIGS. 9, 10, 11, 12, and 13. Such reservoirs as shown in these figures would preferably have additional cutouts in the prefabricated panel assembly panel (73) to facilitate mounting of flexible reservoir bags associated with those embodiments.

One potential problem in transferring an organ for transplant is the large amount of random accelerations incurred during transit. Should a vehicle be utilized that must traverse rough roads, or be subjected to extreme turbulence during flight, it may become difficult to measure the reservoir fluid levels of the perfusion system. Baffles can be employed in both reservoirs (9, 40) to minimize fluid sloshing, and incorrect level readings. This problem can be virtually eliminated by using flexible, completely enclosed and sealed bags, similar to those used in medical applications such as for IV infusion. Constituting a reservoir using a bag-type design will allow a volume range of contained fluid much the same as a fixed geometry reservoir. However, measurement of fluid quantity in the reservoir becomes difficult using such methods as pressure, optical, or capacitive sensing.

If a bag-type reservoir is utilized, the enclosed fluid can be monitored by continuously weighing the reservoir using such means as a load cell, strain gauge, or other electronic means currently seen in the art. Although large fluctuations in load will occur due to dynamic loading, the average force can be used and correlated to actual fluid levels. The average load indication by the load cell can be obtained by averaging the force values in a computer, or in this case the electronic control system (132).

Figure 9:
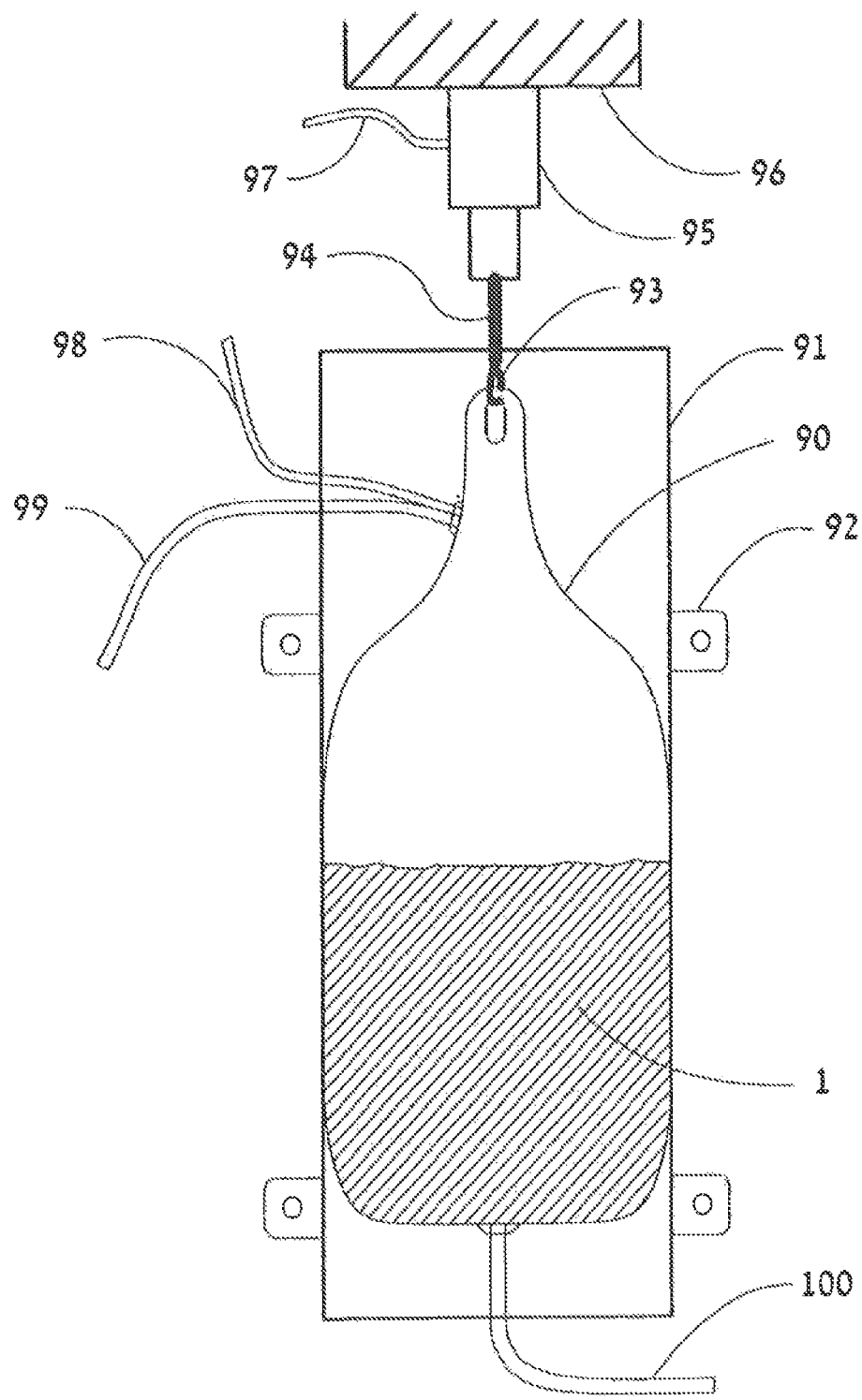
FIG. 9 is a front view of a bag type embodiment of a reservoir according to the present invention.

FIG. 9 shows one embodiment of a bag-style reservoir for determining the quantity of enclosed fluid. A flexible bag (90) is suspended via a clamp, fastener, and/or hook (93), through a cable or other means (94) to a force transducer or load cell (95), for measurement of reservoir weight electronically. The force transducer or load cell (95) is fastened to some fixed structural component of the perfusion system (96). Inlet fluid port (99) allows fluid from the organ to flow into the bag reservoir (90). A second inlet port (98) can be used to both replenish fluid, and act as a reservoir vent, although with a bag-style system there is less need for venting. Perfusion fluid (1) can flow out through the exit tube (100). Measurements of weight are transmitted to the electronic control system (132) via attached wires (97).

Figure 10:
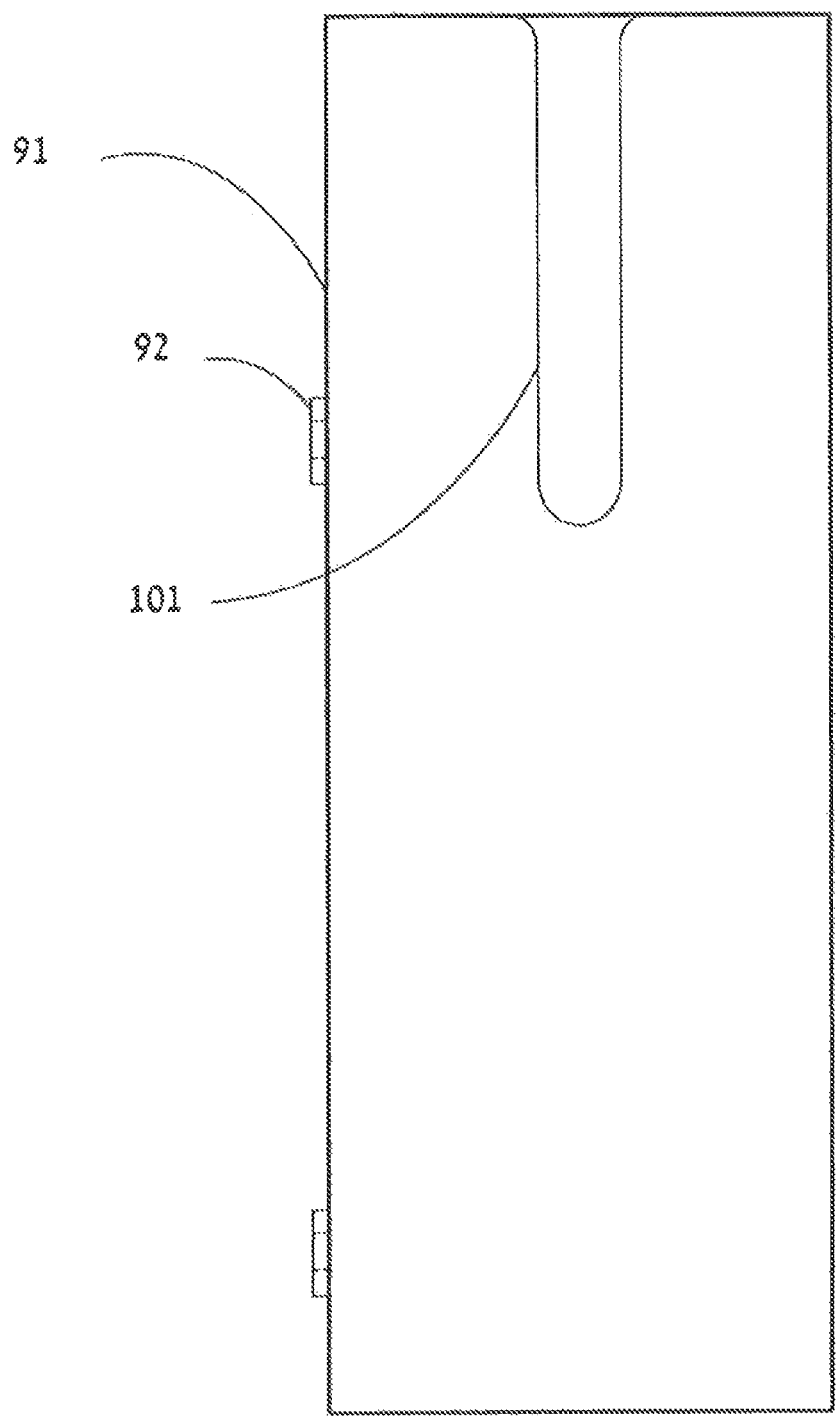
FIG. 10 is a sectional view of the sheath of FIG. 9.

To prevent horizontal movement of the bag due to uncontrollable dynamic loading during transit, a sheath (91) surrounds the bag. This sheath (91) is constructed from a material which exhibits a very low coefficient of friction when in contact with the reservoir bag (90). One good material for this application is Teflon, as it has a very low coefficient of friction, on the order of 0.04 to 0.15 for many common medical fluid-containing materials. It is important that, while containing fluid, that the bag (90) can easily slide vertically inside the sheath (91) to minimize carrying some of the weight load due to friction. FIG. 10 shows a cutout (101) in the sheath (91) allowing the two upper tubes (98, 99) to exit, while maintaining the bag (90) in a horizontally stationary position. Mounting brackets (92) insure that the sheath is fixed and unable to move relative to the entire perfusion system.

Two approaches to incorporating this bag-type reservoir into the previously described prefabricated panel assembly will be shown. One embodiment would be to include the sheath (91) as a component of the prefabricated panel assembly, FIG. 7, attached to the prefabricated panel assembly support panel (73). In this embodiment the bag (90) would be preinstalled inside the sheath (91) as part of the prefabricated panel assembly awaiting the filling of fluid. A less preferred embodiment would be to attach the sheath directly to the perfusion system support structure (71) through an opening (not shown) in the prefabricated panel assembly panel (73), and allow the slit (101) to extend the full length of the sheath for the insertion of the reservoir bag (90) and associated tubing (98, 99) when a new prefabricated panel assembly is installed.

Figure 11:
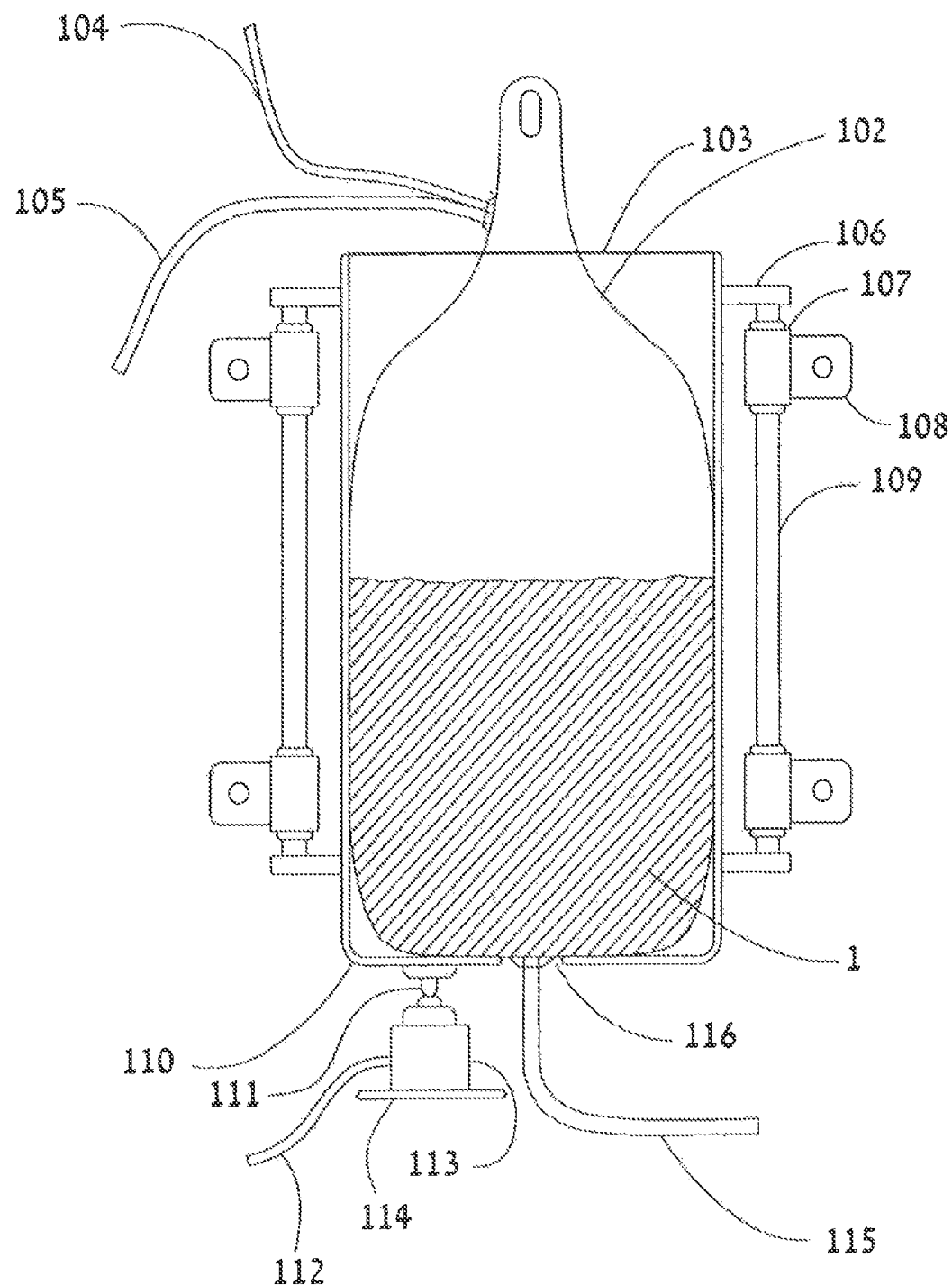
FIG. 11 is a front view of another bag type embodiment of a reservoir according to the present invention.

Yet another embodiment of the weighed-reservoir approach is shown in FIG. 11. A container (110) of structurally appropriate material is used to house the bag reservoir (102) containing perfusion fluid (1). Vertical rails (109) are attached to the container (110) with attachments brackets (106). Linear bearings (107) are used to allow the rails (109) to freely move vertically, while the container (110) is not allowed to rotate or move horizontally. The linear bearings (107) are mounted by brackets (108) which are affixed to the perfusion system's support structure (71). A hole (116) at the bottom of the container (110) allows perfusion fluid (1) to exit the bag (102) through the exit tube (115) to pump-A (15). To facilitate installation of the bag reservoir (102), the hole (116) may be located at the bottom of a vertical slit running from this hole (116) to the top of the container (103), whereas the slit's width is greater than the exit tubing's (115)

diameter for easy insertion. This will allow the installation of the bag (102) as a part of the prefabricated panel assembly without having to cut the tube (115) for installation into the container (110). Perfusion fluid (1) entering the bag reservoir (102) from the organ (2) is accomplished via a tube (105) and venting and replenishment requirements are met through another tube (104).

The total weight of the movable components (110, 111, 102, 106, 109), plus the contained volume of perfusion fluid (1) create a downward force which is transmitted to a load cell (113) through a point of contact (111). The load cell (113) is connected to a fixed part of the perfusion system's structure (114), and the signal from the load cell is sent to the electronic control system (132) via a set of wires (112). The electronic control system (132) simply subtracts the known weight of all of the movable components (110, 111, 102, 106, 109) from the total weight measured, to obtain the fluid weight. As mentioned, the electronic control system (132) averages the readings from the load cell (113) to obtain the reading of fluid volume contained in the reservoir. This technique can be used for both reservoir-A (9) and reservoir-B (40) if needed.

Figure 12:
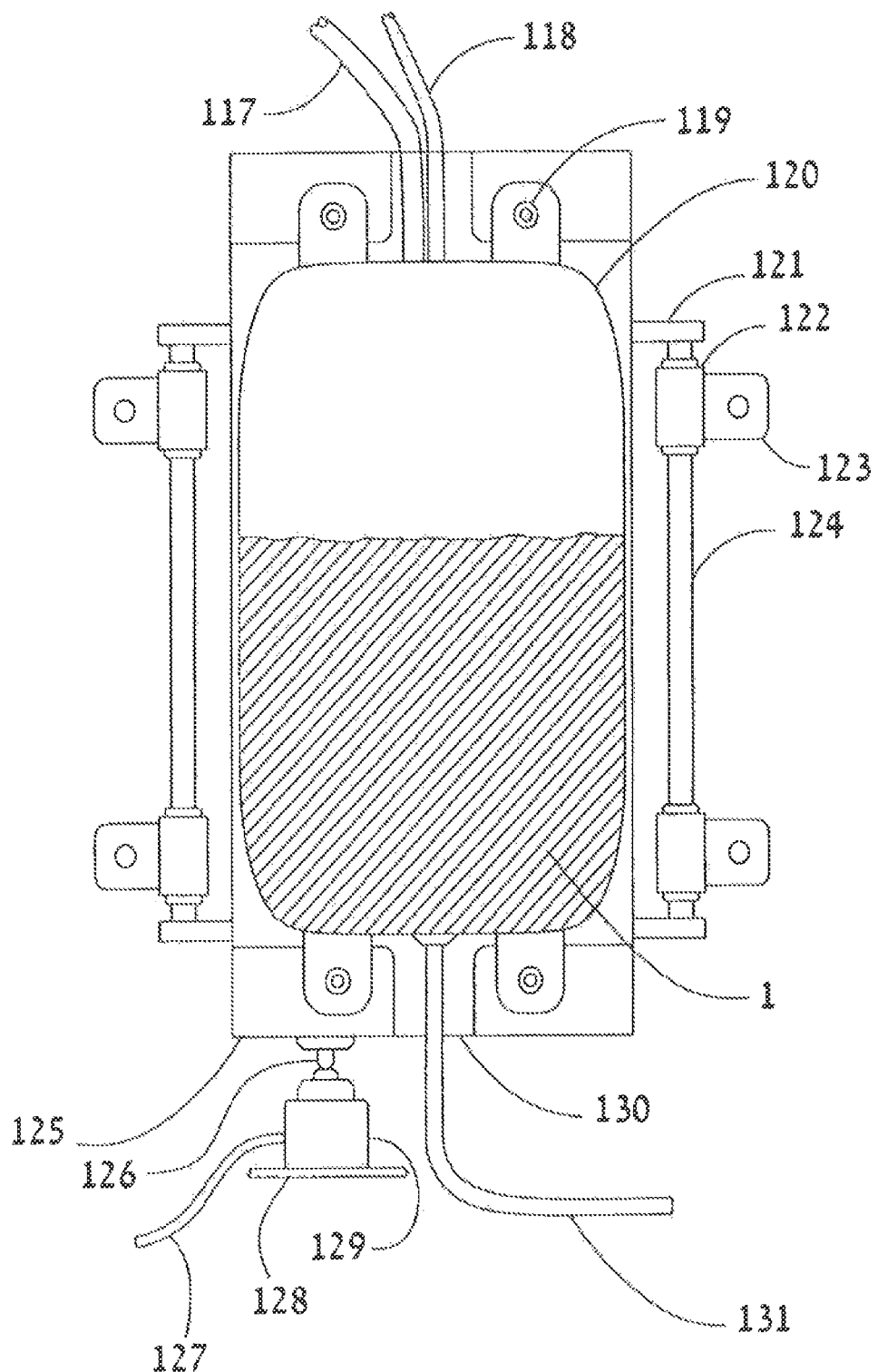
FIG. 12 is front view of yet another bag type embodiment of a reservoir according to the present invention.
Figure 13:
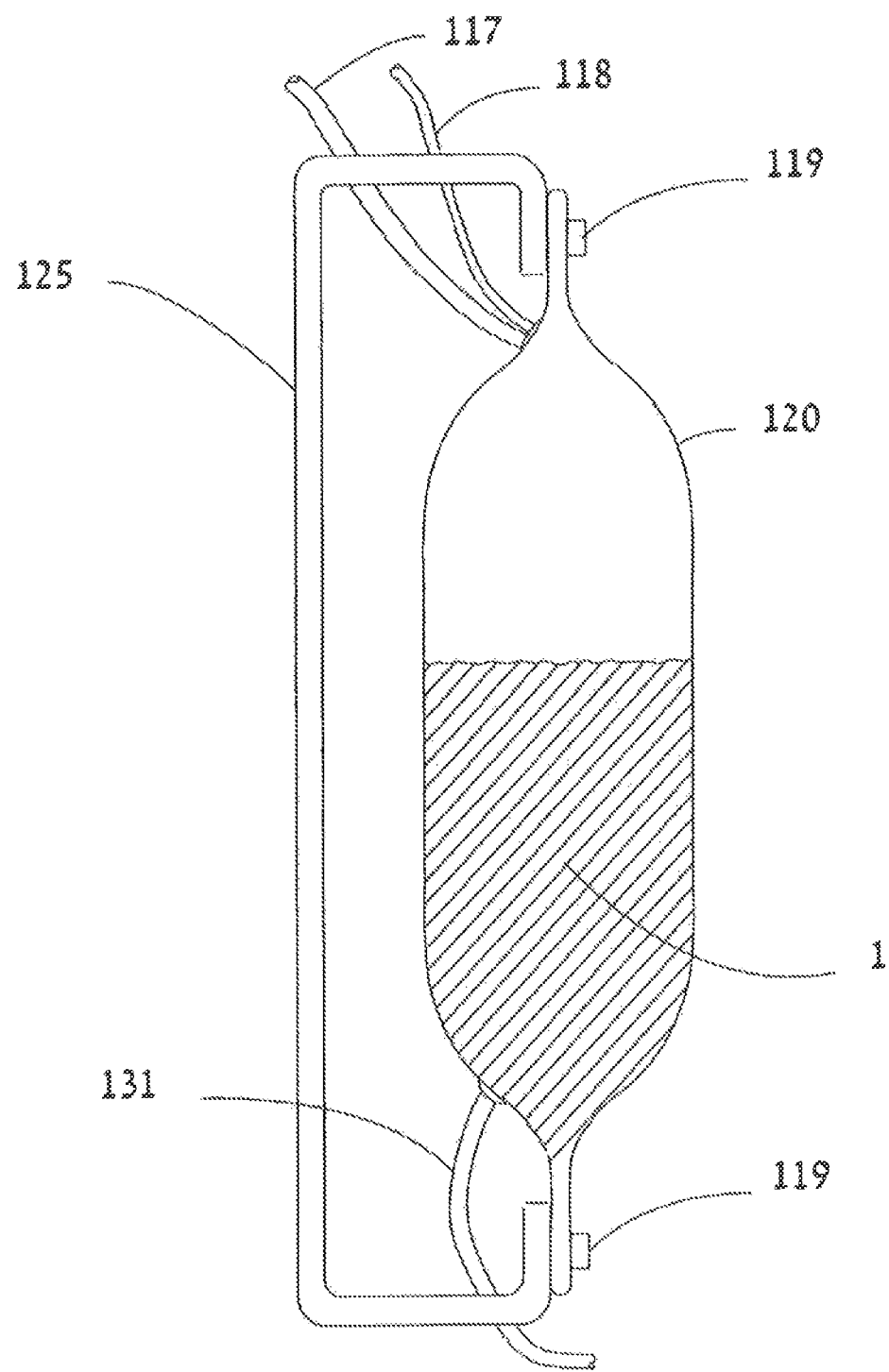
FIG. 13 is a side view of the bag type reservoir of FIG. 12.

The preferred embodiment for incorporating the bag reservoir system into the prefabricated panel assembly is shown in FIGS. 12 and 13. Turning first to FIG. 12, this drawing shows a support bracket (125) as a mounting station to secure the bag reservoir (120) for weighing. This support bracket (125) is attached to rails (124) through mounting brackets (121). The rails (124) move vertically inside linear bearings (122). The linear bearings (122) are attached to the prefabricated panel assembly support panel (71) with mounting brackets (123). A point of contact (126) allows the weight of the bag (120), the support bracket (125), the mounting brackets (121), the rails (124), and the perfusion fluid (1) contained in the bag (120) to be weighed by the load cell (129). The load cell (129) rests on a support structure (128) attached to the prefabricated panel assembly support panel (71). Data from the load cell is sent to the electronic control system (132) via a set or wires (127). The reservoir fluid inlet tube (117) and the vent/replenishment tube (118) are shown in FIG. 12, along with the fluid outlet tube (131). The reservoir bag (120) is attached to the support bracket (125) by screws, bolts, or other fasteners (119). An opening (130) in the support bracket (125) allows easy insertion of the outlet tube (131).

FIG. 13 shows a side view of the bag (120) attached to the support bracket (125) with fasteners (119). Perfusion fluid (1) flows into and out of the bag via inlet tube (117) and outlet tube (131) respectively. The construction of the support bracket allows for easy insertion of all tubing (117, 118, 131).

Figure 14:
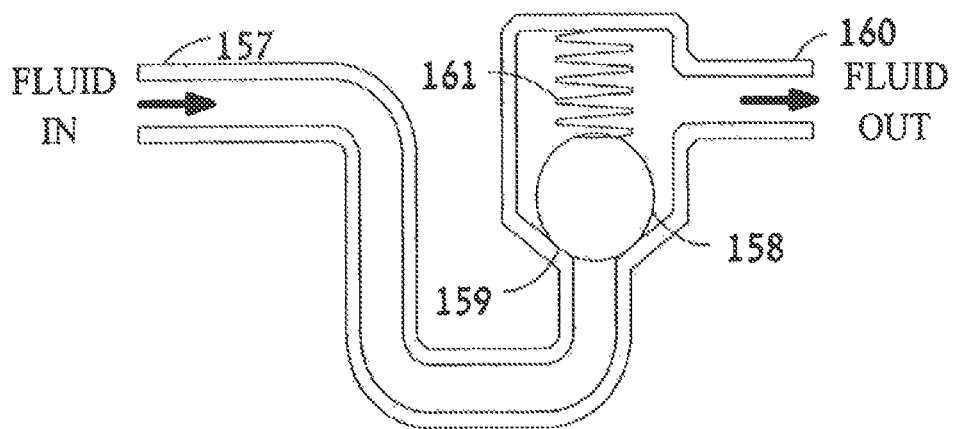
FIG. 14 is a back pressure regulator of a further embodiment of the perfusion system according to the present invention.

An alternate method of creating backpressure on the vein of the organ (2) is shown in FIG. 14. This removes the requirement to have the entry port (8) into reservoir-A (9) at a higher level than the organ's vein (5) by a distance 'h' (6). Perfusion fluid flows out from the vein (5) and into the entry port (157) of a back pressure regulator system. The perfusion fluid (1) is directed to a ball (158) and ball seat (159). In one embodiment, the required backpressure for the organ (2) is adjusted solely by the weight of the ball (158) against the seat (159). When the required pressure is obtained, the ball is lifted from the seat and perfusion fluid (1) is allowed to flow to the exit port of the back pressure regulator (160) which can be at the same level as the reservoir-A entry port (8). The pressure to lift the ball (158) is calculated by taking the weight of the ball (158), while considering the buoyancy of the ball (158) in the perfusion fluid (1), and dividing the balls net weight (weight minus buoyant force) by the area of the seat opening (159). Once the required backpressure is obtained and the ball is lifted, only slightly greater pressures will be seen with considerably larger flow rates.

In the preferred embodiment, a spring (161) can be added to help close the valve without relying on ball weight alone. This is the preferred embodiment due to the fact that the spring (161) is less susceptible to inertial forces seen more often in portable systems. With this approach, the flow can move horizontally rather than upward through the ball seat, as shown in FIG. 14. Virtually any pressure regulating system found in the art will suffice, given that the components can be sterilized easily and not generate excessive contamination, though the disclosed methods are preferable because of their simplicity, small space constraints, and consistent functionality in a likely portable system environment.

Figure 15:
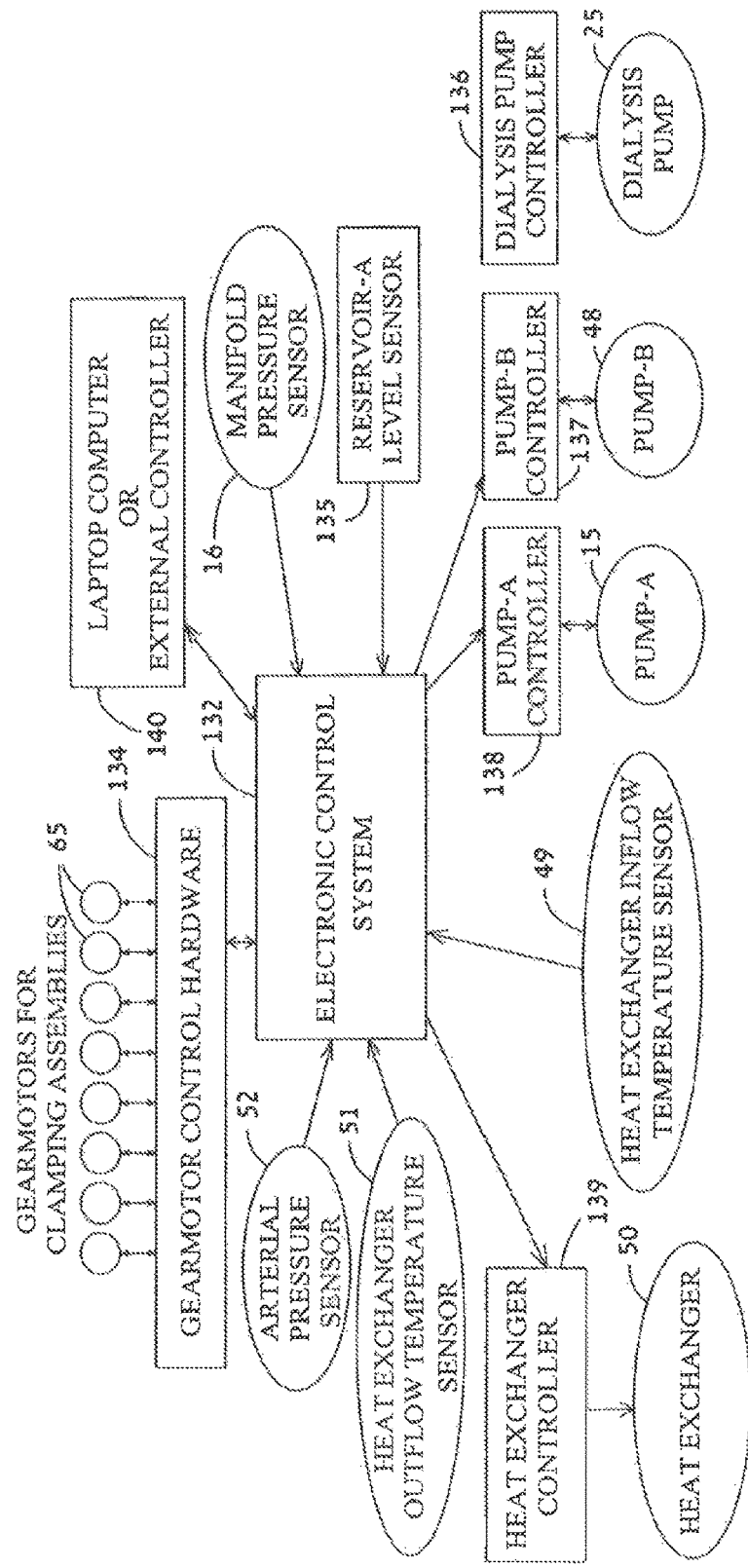
FIG. 15 is a schematic representation of the electronic control system of FIG. 1.

An electronic control system (132) is shown in FIG. 15. This computer-based control and monitoring system can range from an embedded microcontroller to a complete computer system based on similar technology as found in modern laptop or desktop computers. The function of the electronic control system (132) is to monitor, control, and gather data from the various components of the perfusion system. The preferred embodiment of this electronic control system (132) requires all sensor data to pass into the electronic control system (132) for processing. The electronic control system (132) also is responsible for closed loop feedback for controlling temperature and serves as the control system for adjustments in pump speeds.

The electronic control system (132) can be implemented using a microcontroller-type module. Data recording, processing, reporting, and manipulation, along with viewer screen interface options can more easily be performed using a laptop computer or external controller connected to the basic electronic control system (132) via WiFi, Bluetooth, RS-232 com port, USB link, or other suitable interfaces schemes. This makes all but the most basic operations relegated to a modern state of the art computer, equipped with a full range of computer graphics for data display and control. The use of modularity in the addition of a laptop computer or external controller (140) allows for quickly changing out this computer or controller (140) should failure in the hardware (140) occur, adding additional robustness to the portable perfusion system.

All geared stepping motors (65) for the clamping assemblies (19, 21) should be controlled by either the electronic control system (132) directly, or indirectly by hardware, to generate the required stepping sequences for the geared stepping motors (65), along with the monitoring of the motor's position through feedback. Normally these functions are carried out by independent hardware, as would be the case in the preferred embodiment of this perfusion system.

Each geared stepping motor (65) is connected to gearmotor control hardware (134). This control hardware (134) issues the stepping pulses to the geared stepping motors (65) to advance the rotation of each geared stepping motor (65). In-turn, the position feedback to this gear motor control hardware (134) is used to determine the position of each cam assembly (66, 67, 68) to inform the gear motor control hardware (134) as to what position the clamping assembly (19, 21) is in currently, and how many more steps will be necessary to open or close the clamping assembly (19, 21). In this preferred embodiment, the electronic control system (132) only needs to send commands to the gearmotor control hardware (134) to either open or close a specific clamping assembly (19, 21). Feedback from the gearmotor control hardware (134) may be employed to notify the electronic control system (132) of successful completion of the requested open-close operation.

Pump-A (15), pump-B (48), and the dialysis fluid pump (25), are all connected to their respective controller hardware (138, 137, 136), each of which controls the on-off or speed of the motors as necessary. The heat exchanger controller (139) adjusts the rate of heat addition or removal for the heat exchanger (50), Also the heat exchanger controller (139) is responsible for changing the direction of current through the Peltier arrays (61) to provide either heating or cooling of the perfusion fluid (1).

Various sensors such as the manifold pressure sensor (16) the heat exchanger inflow temperature sensor (49), the heat exchanger outflow temperature sensor (51), and the arterial pressure sensor (52) are monitored, as their sensor outputs are fed to the electronic control system (132) through appropriate interface devices and techniques demonstrated widely in the art. Reservoir (9, 40) perfusion fluid (1) levels are also reported to the electronic control system (132) normally through capacitive sensing (10, 11), or weight of fluid contained via load cell (113, 129) techniques.

Data output from this electronic control system (132) could also include vital health measurements from the organ (2) through chemical analysis of the fluid entering or exiting the organ (2). Fluid samples could include pH, glucose levels, dissolved oxygen, and numerous other measurable quantities, and can be taken at any point in the system. If the organ (2) is a kidney, then urinalysis can also be performed, and the results recorded using the same electronic control system (132) utilized for primary system control.

Additional functions of the electronic control system (132) may vary, but could include intelligent monitoring of filter pressures to indicate critical points where switchover to other filter cartridges (18) may need to be made. Control of when, and how much, replenishment of perfusion fluid (1) to be made could also be brought under system control. Control of temperature as a function of time is also a potentially desirable feature relieving the operator of the need, thus reducing error. An almost endless array of data operations can be performed from information maintained and/or generated by the electronic controller. Any of these data operations can be designed and implemented by anyone skilled in the art.

While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, I claim:

1. A perfusion system for a mammalian organ comprising:
a first and a second pump to propel perfusion fluid through one of a closed fluid circuit system and a selectively closeable fluid circuit system that includes an organ artery and an organ vein;
a filter cartridge bank consisting of a plurality of filtration cartridges; and
a first and a second fluid reservoir,
wherein the first fluid reservoir is arranged along the fluid circuit between the first pump and the organ, downstream of the organ;
the second pump is arranged along the fluid circuit between the second fluid reservoir and the organ, upstream of the organ; and
the filter cartridge bank is arranged along the fluid circuit between the first pump and the second fluid reservoir.

2. The perfusion system according to claim 1 wherein the first pump is substantially responsible for supplying the pressures necessary to push perfusion fluid through the filter cartridges, and the second pump is substantially responsible for maintaining a flow rate and pressure to the organ.

3. The perfusion system according to claim 1 wherein the first pump is fluidly between the first fluid reservoir and the filter cartridge bank, and the second fluid reservoir is fluidly between the filter cartridge bank and the second pump.

4. The perfusion system according to claim 1 wherein the plurality of multiple filter cartridges are arranged in parallel and may individually be selectively opened to or closed from a fluid flow.

5. The perfusion system according to claim 1 wherein mechanized clamps selectively open and close fluid flow from one of filter cartridge inlet tubing, filter cartridge outlet tubing, and both filter cartridge inlet tubing and filter cartridge outlet tubing.

6. The perfusion system of claim 5 wherein the mechanized clamp is a rotary cam with end-roller which clamps collapsible tubing to valve close and open the tubing to control flow of perfusion fluid one of into and out of the filter cartridges.

7. The perfusion system according to claim 1 further comprising a heat exchanger that heats and cools the perfusion fluid in the perfusion system.

8. The perfusion system according to claim 7 wherein the heat exchanger is a Peltier semiconductor heating-cooling module.

9. The perfusion system according to claim 7 further comprising a bladder containing perfusion fluid, the bladder exhibiting an enhanced surface area to the heating and cooling conductive surfaces of the heat exchanger.

10. The perfusion system according to claim 7 wherein the bladder may be easily be inserted and removed from the heat exchanger without disconnecting the bladder from the fluid circuit.

11. The perfusion system according to claim 1 wherein a pressure regulator provides a substantially constant backpressure on the organ vein.

12. The perfusion system according to claim 1 further comprising a computer-based electronic control system which regulates, monitors, and controls the perfusion process, along with recording data and acting as a user interface via an external laptop or equivalent computer.

13. The perfusion system according to claim 1 wherein multiple components of the perfusion system are pre-fabricated and located on one single serializable panel capable of being inserted into the profusion system easily and quickly.

14. The perfusion system according to claim 1 further comprising a dialyzer cartridge to remove toxins from the perfusion fluid;
an oxygenator for replenishment of oxygen to the organ;
clamping mechanisms that open and close perfusion fluid pathways;
a drop-in prefabricated panel containing pre-sterilized perfusion components ready for installation into the perfusion system;
an enclosure which houses system components and maintains temperature at or near that of the perfusion fluid pathways contained; and
an electronic control system that controls and monitors perfusion system operation.

\* \* \* \* \*